United States Patent [19]

Honda et al.

[11] Patent Number: 4,665,201
[45] Date of Patent: May 12, 1987

[54] AILANTHONE DERIVATIVES

[75] Inventors: Tadashi Honda, Osaka; Kayoko Imao, Nara; Nobuo Nakatsuka, Osaka; Toshihiro Nakanishi, Osaka, all of Japan

[73] Assignee: Suntory, Limited, Japan

[21] Appl. No.: 691,723

[22] Filed: Jan. 15, 1985

Related U.S. Application Data

[63] Continuation of Ser. No. 421,200, Sep. 22, 1982, abandoned.

[30] Foreign Application Priority Data

Sep. 22, 1981 [JP] Japan .................................. 56-151124

[51] Int. Cl.[4] .......................................... C07D 493/08
[52] U.S. Cl. ................................... 549/275; 549/278; 514/908
[58] Field of Search ................ 514/908, 453; 549/275

[56] References Cited

U.S. PATENT DOCUMENTS 4,203,996  5/1980  Mikolajczak et al. ............... 514/908
4,211,866  7/1980  Matsumura et al. ................. 514/908
4,340,726  7/1982  Simon et al. ........................ 514/908

OTHER PUBLICATIONS

Cancer Treatment Reports, vol. 60(8), Aug. 1976, pp. 1041–1043.
S. M. Krupchan et al., Jour. Med. Chem. (1976), vol. 19(9), pp. 1130–1133.
S. M. Krupchan et al., Jour. Org. Chem., vol. 40, No. 5 (Mar. 7, 1975) pp. 648–656.
John M. Cassady et al., Anticancer Agents Based on Natural Product Models, (1980), pp. 255–269.

Primary Examiner—Norma S. Milestone
Attorney, Agent, or Firm—Sughrue, Mion, Zinn, Macpeak and Seas

[57] ABSTRACT

Novel antineoplastic ailanthone derivatives (IIb) represented by the following formula wherein $R_2$ is $C_5$–$C_{18}$ $\alpha,\beta$-unsaturated acyl group and its related compounds are disclosed.

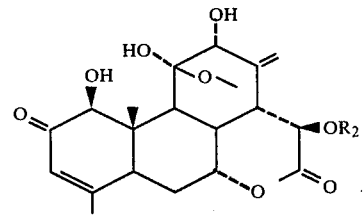

Particularly, some of the above compounds are far more effective than mitomycin C against mouse lymphocytic leucemia p388.

These compounds can be synthesized from known ailanthone via important intermediates, triacyloxy ailanthone, represented by the formula:

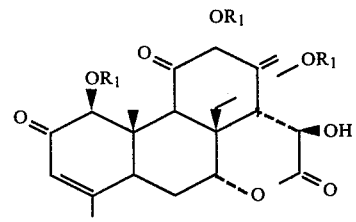

wherein $R_1$ is acyl group.

2 Claims, 1 Drawing Figure

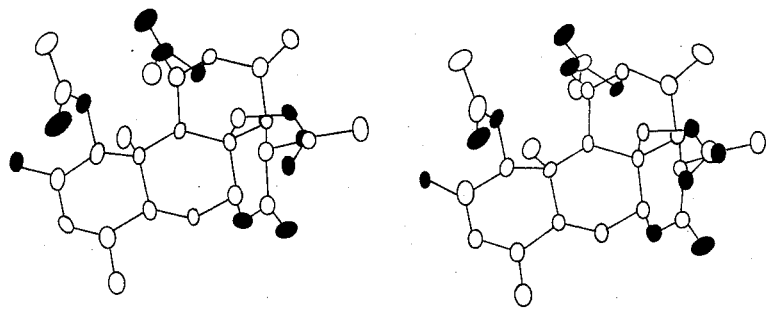

AILANTHONE DERIVATIVES

This is a continuation of application Ser. No. 421,200, filed 9/22/82, now abandoned.

FIELD OF THE INVENTION

This invention relates to novel antineoplastic ailanthone derivatives, and, more particularly, it relates to 15β-hydroxyailanthone-15-carboxylic acid esters represented by the following formulae (IIa and IIb) and a useful intermediate for preparing the above esters represented by the following formula (I); to a method for preparing the compounds (I, IIa and IIb); and to the use of the compounds (IIa and IIb) as an antitumor agent.

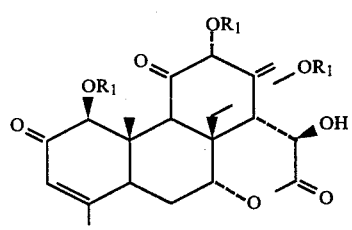

(I)

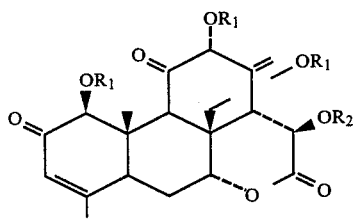

(IIa)

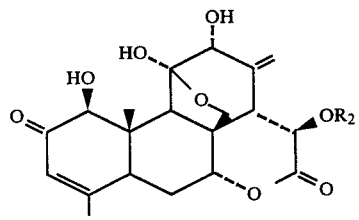

(IIb)

wherein $R_1$ represents acyl group and $R_2$ represents $C_5$–$C_{18}$ α,β-unsaturated acyl group.

BACKGROUND OF THE INVENTION

For the past 30 years, many efforts were continuously made to find antineoplastic agents from natural sources and to synthesize their analogues. As the result, a few of them have been clinically used as antitumor agent. However, effective antitumor agents generally have the defect of high toxicity. Therefore, there is nothing to be satisfied in view of chemotherapy against malignant tumors.

SUMMARY OF THE INVENTION

The present inventors have heretofore noticed to ailanthone (11β,20-epoxy-1β,11α,12α-trihydroxypicrasa-3,13(21)-diene-2,16-dione) represented by the following formula (III), which is contained in the bark of "tree of heaven" (Japanese name "Shinju" or "Niwaurushi"; Ailanthus altissima, Swingle, Simarubaceae), and have synthesized its many derivatives for antineoplastic screening test. Thus, we have found that 15-carboxylic acid esters of 15β-hydroxyailanthone, especially, esters with $C_5$–$C_{18}$ α,β-unsaturated carboxylic acid show marked antineoplastic activity.

For instance, the compounds (I, IIa and IIb) of the present invention can be synthesized from ailanthone (III) as the starting material, according to the following scheme.

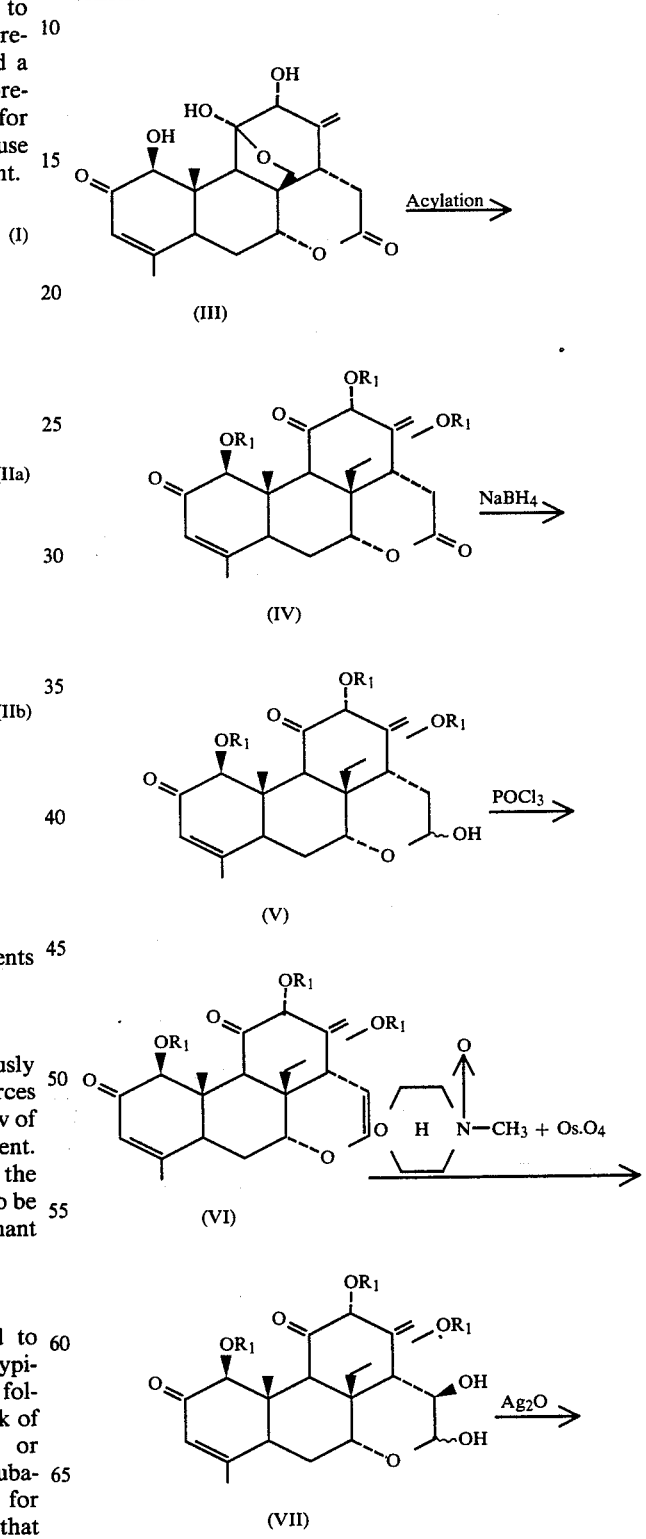

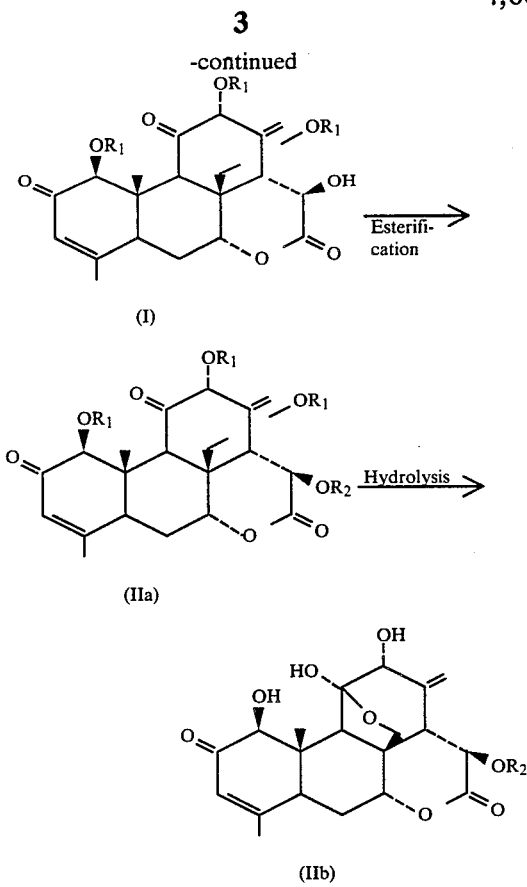

(I)

(IIa)

(IIb)

wherein $R_1$ is acyl group and $R_2$ is $C_5$-$C_{18}$ $\alpha,\beta$-unsaturated acyl group.

That is, ailanthone; (III), which can be extracted and isolated from the bark of "tree of heaven" according to usual manner, is acylated as usual with an acylating agent such as acetic anhydride, acetyl chloride, benzoyl chloride or chloroacetyl chloride to give 1,12,20-triacyloxy compound (IV). During this transformation, C-11 hemiacetal bond is cleaved to give 11-keto-20-alcohol.

Then, the above triacyloxy compound whose alcohol is acylated (IV) is reduced with a selective reducing agent such as sodium borohydride thereby only C-16 ketone of the compound (IV) is selectively reduced to secondary alcohol (V). This alcohol is a mixture of stereoisomers. Then, the alcohol (V) is dehydrated to corresponding compound (VI) with a dehydrating agent such as phosphoryl chloride or phosphorus pentoxide and this unsaturated compound (VI) is further oxidized with N-methylmorpholine-N-oxide and osmium tetraoxide to the corresponding 15,16-dihydroxy compound (VII). Then, the resulting compound (VII) can be converted to 16-ketone compound (I) which is one of the present compounds, by mild oxidation with silver oxide.

Finally, the ketone (I) is esterified with $C_5$-$C_{18}$ $\alpha,\beta$-unsaturated carboxylic acid, cesium fluoride and 1-ethyl-2-fluoropyridinium tetrafluoroborate or 1-methyl-2-fluoropyridinium tosylate to give the desired compound (IIa). Moreover, the compound (IIa) is hydrolyzed with an alkali to give another desired compound (IIb).

The substituent $R_2$ of the compound (IIa) or (IIb) is $C_5$-$C_{18}$ $\alpha,\beta$-unsaturated acyl group such as 3-methyl crotonoyl, cis- or trans-2-pentenoyl, cis- or trans-2-hex- enoyl, cis- or trans-2-heptenoyl, cis- or trans-2-octenoyl, cis- or trans-2-nonenoyl, cis- or trans-2-decenoyl, cis- or trans-2-undecenoyl, cis- or trans-2-dodecenoyl, cis- or trans-2-tridecenoyl, cis- or trans-2-tetradecenoyl, cis- or trans-2-pentadecenoyl, cis- or trans-2-hexadecenoyl, cis- or trans-2-heptadecenoyl, and cis- or trans-2-octadecenoyl groups.

The esterification reaction to give the compound (IIa) can be carried out by several usual manners such as by reacting the compound (I) with an anhydride or a halide of $\alpha$-, $\beta$-unsaturated carboxylic acid or with above acid in the presence of trifluoroacetone as a dehydrating agent. However, according to our experiments, the above reaction with 1-ethyl-2-fluoropyridinium tetrafluoroborate or 1-methyl-2-fluoropyridinium tosylate and cesium fluoride as a dehydrating agent appears to be preferable in view of the yield of the desired compound.

The compound (IIa) can be hydrolyzed to the compound (IIb) under a mild hydrolysis condition. If stronger condition is used, even C-15 ester per se is also hydrolyzed. Therefore, it is preferable that above transformation is carried out in an alcoholic solution of alkali metal alkoxide for a long period of time.

BRIEF DESCRIPTION OF THE DRAWING

The attached drawing is a stereoscopic structural view of 15$\beta$-hydroxy ailanthone triacetate (I:$R_1$=CH$_3$CO—) obtained by X-ray diffraction and computer analysis of the crystal.

DETAILED DESCRIPTION OF THE INVENTION (A) Physico-chemical Data of the Present Compound (i) Compound I ($R_1$=CH$_3$CO—)

Form: colorless needles
mp: 231°–232° C.
Specific rotation (SR): $[\alpha]_D^{25}+20.5°$ (c=0.20, CHCl$_3$)
Infrared spectrum (IR) (KBr, cm$^{-1}$): 3540, 1760, 1740, 1680
Ultraviolet absorption (UV) ($\lambda_{max}^{EtOH}$): 238 nm ($\epsilon$=9000), 203 nm ($\epsilon$=5400)
Proton NMR (NMR) (CDCl$_3$, $\delta$ ppm): 1.41, s(3H, 10—CH$_3$); 1.95, s(3H, 4—CH$_3$); 2.03, 2.08, 2.10, s(each 3H, 3×—OCOCH$_3$); 3.01, brd(1H, 5—H); 3.14, d, J=12 Hz(1H, 14$\beta$—H); 3.18, d, J=2 Hz(1—H, 15$\beta$—OH); 3.56, s(1H, 9$\alpha$—H);

3.56, d, J = 12Hz(1H)
4.52, d, J = 12Hz(1H)  } —CH$_2$—OAc;

4.69, t, (1H, 7$\beta$—H); 5.16, s(1H, 12—H); 5.04, dd, J=2 Hz, 12 Hz(1H, 15$\alpha$—H);

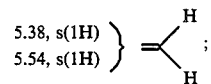
5.38, s(1H)
5.54, s(1H)

5.46, s(1H, 1—H); 6.04, q(1H, 3—H)
Mass spectrum (MS) (m/e): M$^+$518, 476, 458, 416, 392, 374

| Elemental analysis: | C | H |
|---|---|---|
| Found | 60.27 | 5.80 |
| Calcd. | 60.23 | 5.83 |

X-ray diffraction analysis
  R-value: (0.071 except |FOBS|=0)
  Crystallization: Recrystallized from ethanol-water
  Specific gravity: 1.37
  Space group: $P2_1$ (monoclinic) $Z=2$
    lattice constants:
    $a = 10.254$Å ($\sigma(a) = 0.001$)
    $b = 14.560$Å ($\sigma(b) = 0.002$)
    $c = 8.4670$Å ($\sigma(c) = 0.0009$)
    $\beta = 101.45°$ ($\sigma(\beta) = 0.01°$)

(ii) Compound IIa ($R_1 = CH_3CO-$)

General formula

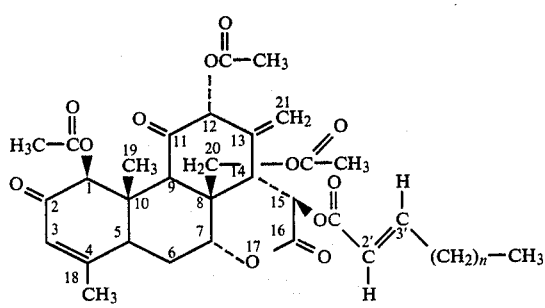

(1) $n = 14$
  Form: amorphous
  SR: $[\alpha]_D^{24} - 2.00°$ (c=0.15, CHCl$_3$)
  IR (KBr, cm$^{-1}$): 1750, 1740, 1730, 1680
  UV ($\lambda_{max}^{EtOH}$): 210 nm, 238 nm
  NMR (CDCl$_3$, $\delta$ ppm): 0.90 (terminal —CH$_3$); 1.28(5'-17'CH$_2$); 1.45(3H, s, 10—CH$_3$); 1.97(3H, s, 4—CH$_3$); 2.04, 2.10, 2.16(3H, s,

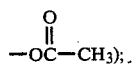

3.12(1H, brd, 5—H); 3.34(1H, d, J=12 Hz, 14—H); 3.58, 4.58(1H, d, J=12 Hz, —CH$_2$—O—); 3.72(1H, s, 9—H); 4.74(1H, t, 7—H); 5.26(1H, s, 12—H); 5.42(1H, s, 1—H); 5.30, 5.50(1H, s,

5.86(1H, dt, J=16, 1 Hz, 2'—H); 6.06(1H, brs, 3—H); 6.28(1H, d, J=12 Hz, 15—H); 7.08(1H, dt, J=16, 7 Hz, 3'—H)
MS (m/e): 782, 740, 698, 680, 638, 514, 490, 472

| Elemental analysis: | C | H |
|---|---|---|
| Found | 67.37 | 7.89 |
| Calcd. | 67.52 | 7.93 |

(2) $n = 13$
  Form: amorphous
  IR (KBr, cm$^{-1}$): 1750, 1740, 1730, 1580
  UV ($\lambda_{max}^{EtOH}$): 210 nm, 238 nm
  NMR (CDCl$_3$, ppm): 1.28(5'-16'CH$_2$)

| Elemental analysis: | C | H |
|---|---|---|
| Found | 67.01 | 7.79 |
| Calcd. | 67.19 | 7.81 |

(3) $n = 12$
  Form: amorphous
  SR: $[\alpha]_D^{23} - 4.35°$ (c=0.23, CHCl$_3$)
  IR (KBr, cm$^{-1}$): 1760, 1750, 1730, 1680
  UV ($\lambda_{max}^{EtOH}$): 210 nm, 238 nm
  NMR (CDCl$_3$, $\delta$ ppm): 1.28 (5'-15'—CH$_2$)

| Elemental analysis: | C | H |
|---|---|---|
| Found | 66.71 | 7.73 |
| Calcd. | 66.84 | 7.69 |

(4) $n = 11$
  Form: amorphous
  IR (KBr, cm$^{-1}$): 1760, 1740, 1730, 1680
  UV ($\lambda_{max}^{EtOH}$): 210 nm, 238 nm
  NMR (CDCl$_3$, $\delta$ ppm): 1.28 (5'-14'—CH$_2$—)

| Elemental analysis: | C | H |
|---|---|---|
| Found | 66.30 | 7.55 |
| Calcd. | 66.49 | 7.57 |

(5) $n = 10$
  Form: amorphous
  SR: $[\alpha]_D^{24} - 1.58°$ (c=0.19, CHCl$_3$)
  IR (KBr, cm$^{-1}$): 1760, 1740, 1730, 1680
  UV ($\lambda_{max}^{EtOH}$): 210 nm, 238 nm
  NMR (CDCl$_3$, $\delta$ ppm): 1.28 (5'-13'—CH$_2$—)
  MS (m/e): 726, 684, 642, 624, 582, 458, 434, 416

| Elemental analysis | C | H |
|---|---|---|
| Found | 66.03 | 7.43 |
| Calcd. | 66.10 | 7.49 |

(6) $n = 9$
  Form: amorphous
  SR: $[\alpha]_D^{24} - 1.18°$ (c=0.17, CHCl$_3$)
  IR (KBr, cm$^{-1}$): 1740, 1730, 1680
  UV ($\lambda_{max}^{EtOH}$): 210 nm, 238 nm
  NMR (CDCl$_3$, $\delta$ ppm): 1.28 (5'-12'—CH$_2$—)
  MS (m/e): 712, 670, 628, 500, 476, 458

| Elemental analysis: | C | H |
|---|---|---|
| Found | 65.80 | 7.34 |
| Calcd. | 65.71 | 7.35 |

(7) $n = 8$
  Form: amorphous
  SR: $[\alpha]_D^{24} - 3.46°$ (c=0.26, CHCl$_3$)
  IR (KBr, cm$^{-1}$): 1760, 1750, 1740, 1680
  UV ($\lambda_{max}^{EtOH}$): 210 nm, 238 nm
  NMR (CDCl$_3$, $\delta$ ppm): 1.28 (5'-11'—CH$_2$—)
  MS (m/e): 698, 656, 638, 614, 596, 458, 434, 416

| Elemental analysis: | C | H |
|---|---|---|
| Found | 65.22 | 7.22 |

-continued

| Elemental analysis: | C | H |
|---|---|---|
| Calcd. | 65.31 | 7.21 |

(8) n=7
Form: amorphous
SR: $[\alpha]_D^{27} -9.38°$ (c=0.16, CHCl$_3$)
IR (KBr, cm$^{-1}$): 1750, 1740, 1680
UV ($\lambda_{max}^{EtOH}$): 210 nm, 238 nm
NMR (CDCl$_3$, δ ppm): 1.28 (5'-10'—CH$_2$—)
MS (m/e): 684, 642, 600, 472, 448, 430

| Elemental analysis: | C | H |
|---|---|---|
| Found | 64.82 | 7.03 |
| Calcd. | 64.91 | 7.02 |

(9) n=6
Form: amorphous
SR: $[\alpha]_D^{27} -7.50°$ (c=0.20, CHCl$_3$)
IR (KBr, cm$^{-1}$): 1760, 1740, 1690
UV ($\lambda_{max}^{EtOH}$): 210 nm, 238 nm
NMR (CDCl$_3$, δ ppm): 1.28 (5'-9'—CH$_2$—)
MS (m/e): 670, 628, 586, 458, 434, 416

| Elemental analysis: | C | H |
|---|---|---|
| Found | 64.24 | 6.88 |
| Calcd. | 64.46 | 6.91 |

(10) n=5
Form: amorphous
SR: $[\alpha]_D^{24} +6.47°$ (c=0.17, CHCl$_3$)
IR (KBr, cm$^{-1}$): 1760, 1740, 1680
UV ($\lambda_{max}^{EtOH}$): 210 nm, 238 nm
NMR (CDCl$_3$, δ ppm): 1.28 (5'-8'—CH$_2$—)
MS (m/e): 656, 614, 572, 444, 420, 402

| Elemental analysis: | C | H |
|---|---|---|
| Found | 63.90 | 6.77 |
| Calcd. | 64.01 | 6.75 |

(11) n=4
Form: amorphous
IR (KBr, cm$^{-1}$): 1760, 1750, 1730, 1680
UV ($\lambda_{max}^{EtOH}$): 210 nm, 238 nm
NMR (CDCl$_3$, δppm): 1.28 (5'-7'—CH$_2$—)

| Elemental analysis: | C | H |
|---|---|---|
| Found | 63.36 | 6.56 |
| Calcd. | 63.54 | 6.59 |

(12) n=3
Form: amorphous
IR (KBr, cm$^{-1}$): 1760, 1730, 1680
UV ($\lambda_{max}^{EtOH}$): 210 nm, 238 nm
NMR (CDCl$_3$, δppm): 1.28 (5'-6'—CH$_2$—)

| Elemental analysis: | C | H |
|---|---|---|
| Found | 62.91 | 6.33 |
| Calcd. | 63.06 | 6.37 |

(13) n=2

(14)
Form: amorphous
IR (KBr, cm$^{-1}$): 1760, 1750, 1730, 1680
UV ($\lambda_{max}^{EtOH}$): 210 nm, 238 nm
NMR (CDCl$_3$, δppm): 1.28 (5'—CH$_2$—)

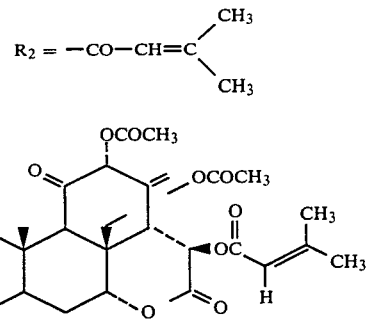

Form: amorphous
IR (KBr, cm$^{-1}$): 1760, 1750, 1730, 1680
NMR (CDCl$_3$, δppm): 1.45(10—CH$_3$); 1.95(4—CH$_3$);
2.04, 2.10, 2.17

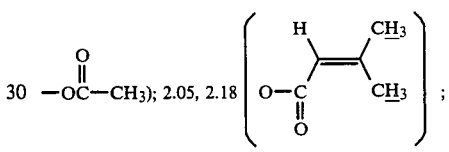

$\left.\begin{array}{l}3.58, d, J = 12Hz \\ 4.58, d, J = 12Hz\end{array}\right\}$ (CH$_2$O—); 3.72(s, 9—H); 4.74(t, 7—H); 5.24(s, 12—H);
5.31, 5.50

5.42(s, 1-H); 5.72(t, 2—H); 6.05(brs, 3—H); 6.26(d, J=12 Hz, 15—H)

| Elemental analysis: | C | H |
|---|---|---|
| Found | 61.90 | 6.03 |
| Calcd. | 62.01 | 6.02 |

(iii) Compound, IIa (R$_1$=CH$_3$CO—)
General formula

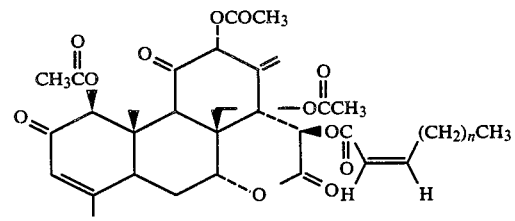

(1) n=7
Form: amorphous

SR: $[\alpha]_D^{26} -22.3°$ (c=0.39, CHCl$_3$)
IR (KBr, cm$^{-1}$): 1750, 1690
UV ($\lambda_{max}^{EtOH}$): 213 nm ($\epsilon$=19200), 240 nm(sh)($\epsilon$=12800)
NMR (CDCl$_3$, δppm): 0.84(3H, t, terminal—CH$_3$); 1.42(3H, s, 10—CH$_3$); 1.93(3H, s, 4—CH$_3$); 2.00, 2.07, 2.13(each 3H, s,

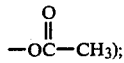
);

3.08(1H, brd, 5—H); 3.28(1H, d, J=12 Hz, 14—H); 3.56, 4.56(each 1H, d, J=12 Hz, —CH$_2$O—); 3.67(1H, s, 9—H); 4.70(1H, t, 7—H); 5.20(1H, s, 12—H); 5.27, 5.47(each 1H, s,

);

5.40(1H, s, 1—H); 5.76(1H, dt, J=12 Hz, 2'—H); 6.02(1H, brs, 3—H); 6.24(1H, d, J=12 Hz, 15—H); 6.36(1H, dt, J=12 Hz, 8 Hz, 3'—H)
MS (m/e): 684(M$^+$), 642, 600, 458, 416

| Elemental analysis: | C | H |
|---|---|---|
| Found | 65.01 | 7.17 |
| Calcd. | 64.89 | 7.07 |

(2) n=0
Form: amorphous
SR: $[\alpha]_D^{26} -23.8°$ (c=0.24, CHCl$_3$)
IR (KBr, cm$^{-1}$): 1750, 1690
UV ($\lambda_{max}^{EtOH}$): 213 nm ($\epsilon$=19600), 240 nm(sh)($\epsilon$=12600)
NMR (CDCl$_3$, δ ppm): 0.84(3H, t, terminal —CH$_3$); 1.42(3H, s, 10—CH$_3$); 1.93(3H, s, 4—CH$_3$); 2.00, 2.07, 2.13(each 3H, s,

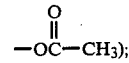
);

3.08(1H, brd, 5—H); 3.28(1H, d, J=12 Hz, 14—H); 3.56, 4.56(each, 1H, d, J=12 Hz, —CH$_2$O—); 3.67(1H, s, 9—H); 4.70(1H, t, 7—H); 5.20(1H, s, 12—H); 5.27, 5.47(each 1H, s,

);

5.40(1H, s, 1—H); 5.76(1H, dt, J=12 Hz, 1 Hz, 2'—H); 6.02(1H, brs, 3—H); 6.24(1H, d, J=12 Hz, 15—H); 6.36(1H, dt, J=12 Hz, 8 Hz, 3'—H)
MS (m/e): 726(M$^+$), 684, 642, 458, 416

| Elemental analysis: | C | H |
|---|---|---|
| Found | 66.29 | 7.32 |
| Calcd. | 66.10 | 7.49 |

(iv) Compound, IIb
General formula

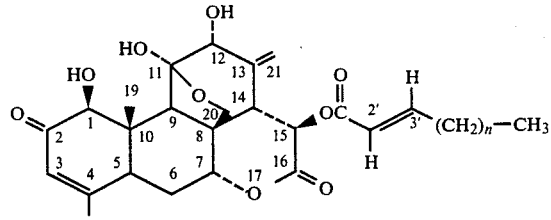

(1) n=14
Form: amorphous
SR: $[\alpha]_D^{27} +56.1°$ (c=0.13, CHCl$_3$)
IR (KBr, cm$^{-1}$): 3250, 1760, 1730, 1670
UV ($\lambda_{max}^{EtOH}$): 214 nm, 238 nm
NMR (CDCl$_3$, δ ppm): 0.90 (terminal—CH$_3$); 1.23(3H, s, 10—CH$_3$); 1.28(brs, 5'-17'CH$_2$); 2.04(3H, s, 4—CH$_3$); 3.08(1H, s, 9—H); 3.55, 3.93 (1H, d, J=8 Hz, —CH$_2$O—); 4.07(1H, s, 12—H); 4.21(1H, s, 1—H); 4.63(1H, t, 7—H); 5.87(1H, dt, J=16 Hz, 1 Hz, 2'—H); 5.18, 5.36(1H, s,

);

5.73(1H, d, J=11 Hz, 15—H); 6.16(1H, brs, 3—H); 7.06(1H, dt, J=16 Hz, 7 Hz, 3'—H)
MS (m/e): 656, 638, 612, 568

| Elemental analysis: | C | H |
|---|---|---|
| Found | 68.68 | 8.33 |
| Calcd. | 68.76 | 8.34 |

(2) n=13
Form: amorphous
IR (KBr, cm$^{-1}$): 3300, 1760, 1730, 1670
UV ($\lambda_{max}^{EtOH}$): 214 nm, 238 nm
NMR (CDCl$_3$, δ ppm): 1.28(brs, 5'-16'—CH$_2$—)

| Elemental analysis: | C | H |
|---|---|---|
| Found | 69.01 | 8.45 |
| Calcd. | 69.13 | 8.47 |

(3) n=12
Form: amorphous
SR: $[\alpha]_D^{23} +50.0°$ (c=0.15, CHCl$_3$)
IR (KBr, cm$^{-1}$): 3300, 1760, 1730, 1670
UV ($\lambda_{max}^{EtOH}$): 214 nm, 238 nm
NMR (CDCl$_3$, δ ppm): 1.28(brs, 5'-15'—CH$_2$—)
MS (m/e): 628, 610, 600, 586, 568, 558, 556, 540
High resolution MS: Found m/e 628.3595
(Calcd. for C$_{36}$H$_{52}$O$_9$, m/e 628.3610)

| Elemental analysis: | C | H |
|---|---|---|
| Found | 68.68 | 8.33 |
| Calcd. | 68.76 | 8.34 |

(4) n=11
Form: amorphous
IR (KBr, cm$^{-1}$): 3310, 1760, 1730, 1670
UV ($\lambda_{max}^{EtOH}$): 214 nm, 238 nm
NMR (CDCl$_3$, δ ppm): 1.28(brs, 5'-14'—CH$_2$—)

| Elemental analysis: | C | H |
|---|---|---|
| Found | 68.19 | 8.18 |
| Calcd. | 68.38 | 8.20 |

(5) n=10
Form: amorphous
SR: $[\alpha]_D^{23}+38.2°$ (c=0.11, CHCl$_3$)
IR (KBr, cm$^{-1}$): 3320, 1760, 1730, 1670
UV ($\lambda_{max}^{EtOH}$): 214 nm, 238 nm
NMR (CDCl$_3$, δ ppm): 1.28($5^1$-$13^1$—CH$_2$—)
MS (m/e): 600, 582, 572, 558, 516, 512, 434, 416

| Elemental analysis: | C | H |
|---|---|---|
| Found | 67.81 | 8.07 |
| Calcd. | 67.98 | 8.05 |

(6) n=9,
Form: amorphous
SR: $[\alpha]_D^{25}+37.9°$ (c=0.28, CHCl$_3$)
IR (KBr, cm$^{-1}$): 3300, 1760, 1730, 1670
UV ($\lambda_{max}^{EtOH}$): 214 nm, 238 nm
NMR (CDCl$_3$, δ ppm): 1.28(5'-12'—CH$_2$—)

| Elemental analysis: | C | H |
|---|---|---|
| Found | 67.40 | 7.87 |
| Calcd. | 67.55 | 7.90 |

(7) n=8
Form: amorphous
SR: $[\alpha]_D^{23}+49.2°$ (c=0.12, CHCl$_3$)
IR (KBr, cm$^{-1}$): 3300, 1760, 1730, 1670
UV ($\lambda_{max}^{EtOH}$): 214 nm, 238 nm
NMR (CDCl$_3$, δ ppm): 1.28(5'-11'—CH$_2$—)
High resolution MS: Found m/e 572.2940
(Calcd. for C$_{32}$H$_{44}$O$_9$, m/e 572.2983)

| Elemental analysis: | C | H |
|---|---|---|
| Found | 66.98 | 7.74 |
| Calcd. | 66.61 | 7.74 |

(8) n=7
Form: amorphous
SR: $[\alpha]_D^{23}+36.0°$ (c=0.15, CHCl$_3$)
IR (KBr, cm$^{-1}$): 3250, 1760, 1730, 1670
UV ($\lambda_{max}^{EtOH}$): 214 nm, 238 nm
MS (m/e): 558, 540, 530, 516, 486, 470
High resolution MS: Found m/e 558.2807
(Calcd. for C$_{31}$H$_{42}$O$_9$, m/e 558.2825)

| Elemental analysis: | C | H |
|---|---|---|
| Found | 66.45 | 7.58 |
| Calcd. | 66.65 | 7.58 |

(9) n=6
Form: amorphous
SR: $[\alpha]_D^{27}+53.0°$ (c=0.20, CHCl$_3$)
IR (KBr, cm$^{-1}$): 3250, 1750, 1720, 1660
UV ($\nu_{max}^{EtOH}$): 214 nm, 238 nm
NMR (CDCl$_3$, δ ppm): 1.28(brs, 5'-9'—CH$_2$—)
MS (m/e): 544, 526, 516, 502, 498, 472, 458, 456
High resolution MS: Found m/e 544.2694
(Calcd. for C$_{30}$H$_{40}$O$_9$, m/e 544.2672)

| Elemental analysis: | C | H |
|---|---|---|
| Found | 66.07 | 7.39 |
| Calcd. | 66.16 | 7.40 |

(10) n=5
Form: amorphous
SR: $[\alpha]_D^{23}+45.0°$ (c=0.16, CHCl$_3$)
IR (KBr, cm$^{-1}$): 3300, 1760, 1730, 1660
UV ($\lambda_{max}^{EtOH}$): 214 nm, 238 nm
NMR (CDCl$_3$, δ ppm): 1.28(brs, 5'-8'—CH$_2$—)
MS (m/e): 530, 512, 502, 488, 458, 442
High resolution MS: Found m/e 530,2510
(Calcd. for C$_{29}$H$_{38}$O$_9$, m/e 530.2513)

| Elemental analysis: | C | H |
|---|---|---|
| Found | 65.50 | 7.19 |
| Calcd. | 65.64 | 7.22 |

(11) n=4
Form: amorphous
IR (KBr, cm$^{-1}$): 3300, 1760, 1730, 1660
UV ($\lambda_{max}^{EtOH}$): 214 nm, 238 nm
NMR (CDCl$_3$, δ ppm): 1.28(brs, 5'-7'—CH$_2$—)

| Elemental analysis: | C | H |
|---|---|---|
| Found | 64.93 | 6.95 |
| Calcd. | 65.11 | 6.98 |

(12) n=3
Form: amorphous
IR (KBr, cm$^{-1}$): 3310, 1760, 1730, 1660
UV ($\lambda_{max}^{EtOH}$): 214 nm, 238 nm
NMR (CDCl$_3$, δ ppm): 1.28(brs, 5'-6'—CH$_2$—)

| Elemental analysis: | C | H |
|---|---|---|
| Found | 64.29 | 6.79 |
| Calcd. | 64.53 | 6.82 |

(13) n=2
Form: amorphous
IR (KBr, cm$^{-1}$): 3300, 1750, 1730, 1660
UV ($\lambda_{max}^{EtOH}$): 214 nm, 238 nm
NMR (CDCl$_3$, δ ppm): 1.28(brs, $5^1$—CH$_2$—)

| Elemental analysis: | C | H |
|---|---|---|
| Found | 63.78 | 6.58 |
| Calcd. | 63.28 | 6.60 |

(14)

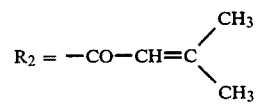

$R_2 =$ —CO—CH=C$\begin{smallmatrix}CH_3\\CH_3\end{smallmatrix}$

-continued

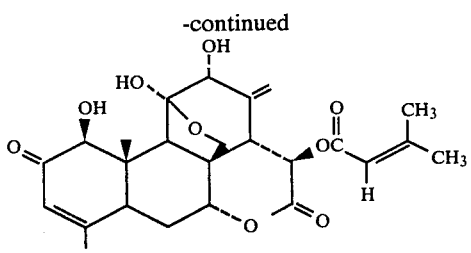

Form: Colorless needles
mp: 168°–169° C.
SR: $[\alpha]_D^{24}+56.1°$ (c=0.38, CHCl$_3$)
IR (KBr, cm$^{-1}$): 3400, 1740, 1720, 1670
UV ($\lambda_{max}^{EtOH}$): 218 nm ($\epsilon$=24500)
NMR (CDCl$_3$, δ ppm): 1.94, 2.19

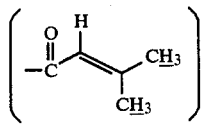

MS (m/e): 474, 456, 446, 432, 402, 386, 374
High resolution MS: Found m/e 474.1907
(Calcd. for C$_{25}$H$_{30}$O$_9$, m/e 474.1890)

| Elemental analysis: | C | H |
|---|---|---|
| Found | 63.11 | 6.29 |
| Calcd. | 63.28 | 6.37 |

(v) Compound, IIb

General formula

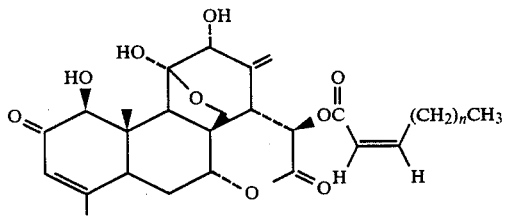

(1) n=7
Form: amorphous
SR: $[\alpha]_D^{26}+50.0°$ (c=0.10, CHCl$_3$)
IR (KBr, cm$^{-1}$): 3300, 1750, 1720, 1660
UV ($\lambda_{max}^{EtOH}$): 216 nm ($\epsilon$=18700), 240 nm(sh) ($\epsilon$=10200)
NMR (CDCl$_3$, δppm): 0.84(3H, t, terminal—CH$_3$); 1.16(3H, s, 10—CH$_3$); 2.00(3H, s, 4—CH$_3$); 3.02(1H, s, 9—H); 3.50, 3.89(1H, d, J=8 Hz, —CH$_2$O—); 4.01(1H, s, 12—H); 4.12(1H, s, 1—H); 4.59(1H, t, 7—H); 5.13, 5.32(each 1H, s,

5.66(1H, d, J=11 Hz, 15—H); 5.80(1H, dt, J=12 Hz, 1 Hz, 2'—H); 6.12(1H, brs, 3—H); 6.34(1H, dt, J=12 Hz, 8 Hz, 3'—H)
MS (m/e): 558, 540, 530, 514, 485, 470

High resolution MS: Found m/e 558.2841
Calcd, for C$_{31}$H$_{42}$O$_9$, m/e 558.2828

(2) n=10
Form: amorphous
SR: $[\alpha]_D^{26}+41.3°$ (c=0.15, CHCl$_3$)
IR (KBr, cm$^{-1}$): 3300, 1750, 1720, 1660
UV ($\lambda_{max}^{EtOH}$): 217 nm($\epsilon$=17900), 240 nm($\epsilon$=11300)
NMR (CDCl$_3$, δppm): 0.84(3H, t, terminal—CH$_3$); 1.16(3H, s, 10—CH$_3$); 2.00(3H, s, 4—C H$_3$); 3.02(1H, s, 9—H); 3.50, 3.89(1H, d, J=8 Hz, —CH$_2$O—); 4.01(1H, s, 12—H); 4.12(1H, s, 1—H); 4.59(1H, t, 7—H); 5.13, 5.32(each 1H, s,

5.66(1H, d, J=11 Hz, 15—H); 5.80(1H, dt, J=12 Hz, 1 Hz, 2'—H); 6.12(1H, brs, 3—H); 6.34(1H, dt, J=12 Hz, 8 Hz, 3'—H)
MS (m/e): 600(M+), 582, 572, 556, 527, 512
High resolution MS: Found m/e 600.3298
Calcd. for C$_{34}$H$_{48}$O$_9$, m/e 600.3298

PREPARATION OF COMPOUNDS

As hereinbefore described, the compounds (I, IIa and IIb) can be derived from known ailanthone (III) as follows:

EXAMPLE 1

Ailanthone triacetate (1,12,20-triacetyl ailanthone)-(IV)

87.4 g (0.23M) of ailanthone was dissolved in 870 ml of anhydrous pyridine and 1700 ml of acetic anhydride was added to the solution. The reaction mixture was allowed to stand for 20 hours at room temperature and then evaporated in vacuo to precipitate out a crystalline substance. This crystalline substance was recrystallized from methanol to give 108.6 g (yield 93%) of compound (IV) as colorless needles. This compound was in agreement with known ailanthone triacetate in view of its physico-chemical data and further it did not show any melting point depression in the mix-melting test with the authentic sample of compound (IV).

EXAMPLE 2

16-hydroxyailanthone-triacetate(1,12,20-triacetylailanthone-16-ol)(V)

15 g (30 mM) of ailanthone triacetate was dissolved in the mixed solvent containing 1.5 l of each of tetrahydrofurane and ethanol. To the solution, 2.25 g (60 mM) of sodium borohydride was added under ice-cooling. The reaction mixture was stirred for 2 hours under ice-cooling and thereafter a saturated aqueous ammonium chloride solution was added. Then, water was added so as to redissolve the formed precipitates and the organic solvent was evaporated in vacuo. The remaining liquid was extracted five times with methylene chloride and fractioned solvent layers were washed twice with water, then washed with saturated salt solution and finally dried over anhydrous magnesium sulfate. This dried extract was then evaporated in vacuo to give 14.7 g of the compound (V) as colorless powder. Yield: 98%
Form: amorphous
SR: $[\alpha]_D^{24}+5.00°$ (c=0.14, CHCl$_3$)
IR (KBr, cm$^{-1}$): 3450, 1750, 1740, 1680

MS (m/e): M+ 504, 462, 444, 420, 402, 378, 360
High resolution MS: Found m/e 504.2013
Calcd. for $C_{26}H_{32}O_{10}$ m/e 504.1996)

| Elemental analysis: | C | H |
|---|---|---|
| Found | 61.76 | 6.39 |
| Calcd. | 61.89 | 6.39 |

EXAMPLE 3

15,16-dehydroailanthone-triacetate(1,12,20-triacetylailanthone-15-ene)(VI)

3.48 g (6.9 mM) of compound (V) was dissolved in 35 ml of pyridine and to the solution thus obtained 2.1 g (12.9 mM) of phosphoryl chloride was added. The reaction mixture was refluxed for 5 minutes under argon atmosphere, followed by addition of ice in order to quench the reaction, and then pyridine was evaporated in vacuo. The remaining oily residue was diluted with water and extracted five times with ethyl acetate. The fractioned organic solvent layers were joined together and washed twice with saturated salt solution followed by drying over anhydrous sodium sulfate. The dried extract was condensed in vacuo to yield colorless crystals. The crystals were recrystallized from ethanol to give 2.01 g of the desired compound (VI) as colorless crystals. Yield: 60%

Form: colorless needles
mp: 186°–187° C.
SR: $[\alpha]_D^{25} -2.86°$ (c=0.21, $CHCl_3$)
IR (KBr, $cm^{-1}$): 1760, 1680
UV ($\lambda_{max}^{EtOH}$): 206 nm($\epsilon$=12000), 238 nm($\epsilon$=11400)
NMR ($CDCl_3$, $\delta$ppm): 1.44, s(3H, 10—$CH_3$); 1.94, s(3H, 4—$CH_3$); 2.04, s(9H, —OAcX3); 3.24, d(1H, 5α—H); 3,44, t(1H, 14β—H); 3.68, s(1H, 9α—H);

$$\left.\begin{array}{l}3.62, d, J = 12Hz\ 1H \\ 4.64, d, J = 12Hz\ 1H\end{array}\right\}$$

(—$CH_2$—OAc); 4.16, t(1H, 7β—H); 4.66, dd, J=7 Hz, 3 Hz (1H, 15—H); 5.15, s(1H, 12—H); 5.24, s(1H, 1—H);

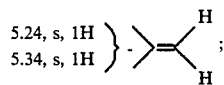

$$\left.\begin{array}{l}5.24, s, 1H \\ 5.34, s, 1H\end{array}\right\}$$

5.98 q J=1 Hz (1H, 3—H); 6.41, dd, J=3 Hz, 7 Hz (1H, 16—H)
MS (m/e): M+ 486, 444, 426, 402, 384, 360, 342

| Elemental analysis: | C | H |
|---|---|---|
| Found | 64.08 | 6.20 |
| Calcd. | 64.19 | 6.22 |

EXAMPLE 4

15,16-dihydroxyailanthone-triacetate(1,12,20-triacetylailanthone-15,16-diol)(VII)

First, a solution of an oxidizing agent was prepared in the following manner: 5.06 g (43 mM) of N-methylmorpholine N-oxide was dissolved in a mixture containing 72.5 ml of water and 29.0 ml of acetone. To this solution, 21.8 mg (0.0857 mM) of osmium tetroxide in 10 ml of t-butanol was added to give the desired solution of the oxidizing agent.

To the above oxidized solution, 13.45 g (17.6 mM) of 1,12,20-triacetylailanthone-15-ene (VI) was added and the resulting solution was diluted with 145 ml of acetone. The reaction mixture was stirred at room temperature for 24 hours, followed by further addition of 290 mg (2.79 mM) of sodium hydrogen sulfite. Then water was poured into the mixture, whereby the solution was homogenized. The solution thus obtained was then condensed in vacuo and the residue was adjusted to pH 2 with 2N HCl. The residue was then saturated with salt, and extracted 5 times with ethyl acetate and the combined extract was then dried over anhydrous sodium sulfate. The dried extract was then evaporated in vacuo to give the diol compound (VII) as colorless powder. (This compound was a mixture of C-16 stereoisomers so that it was impossible to be crystallized.)

The above powder was then chromatographed on 25 g of silica gel (CC-7) (prepared by Mallinckrodt Co.) and eluted with ethyl acetate to obtain 13 g of pure product. Yield: 90%

Form: amorphous
SR: $[\alpha]_D^{25} +3.81°$ (c=0.21, $CHCl_3$)
IR ($cm^{-1}$): 3450, 1760, 1740, 1680
MS (m/e): $M^{30}$ 520, 502, 478, 460, 436, 418, 400, 376, 358
High resolution MS: Found m/e 520.1958
Calcd. for $C_{26}H_{32}O_{11}$ m/e 520.1943

| Elemental analysis: | C | H |
|---|---|---|
| Found | 59.82 | 6.21 |
| Calcd. | 59.99 | 6.20 |

EXAMPLE 5

15β-hydroxyailanthone-triacetate(1,12,20-triacetylailanthone-15β-ol)(I)

17.4 g (33.4 mM) of diol compound (VII) was dissolved in 850 ml of anhydrous acetonitrile, followed by the addition of 52.2 g (421 mM) of activated silver oxide. The mixture was refluxed for 1 hour. After cooling to room temperature, the silver salt was removed from the mixture with cerite. Evaporation of the solvent from the reaction mixture gave 22.6 g of an oily substance. This substance was chromatographed on 300 g of above-described silica gel (CC-7) and eluted with the mixture of ethyl acetate and chloroform (4:6 by volume). The eluate was condensed and the residue was recrystallized from acetone-ether mixture to give 10.4 g of 1,12,20-triacetylailanthone-15β-ol (I). The overall yield of the compound (I) from compound (IV) was 31.7%.

EXAMPLE 6

15β-hydroxyailanthone triacetate-α,β-unsaturated carboxylic acid esters (IIa)

The compound (IIa) of the present invention can be prepared from the above compound (I) by the following general procedure.

1.24 equivalent of an α,β-unsaturated carboxylic acid and 1.50 equivalent of 1-ethyl-2-fluoropyridinium tetrafluoroborate or 1-methyl-2-fluoropyridinium tosylate were dissolved in anhydrous methylene chloride and 4.87 equivalent of cesium fluoride was added thereto.

This solution was then stirred for 30 minutes at room temperature. To this solution, 1.00 g (1.93 mM) of compound (I) (15β-hydroxyailanthonetriacetate was added in one portion. The mixture was then further stirred at room temperature for 20 hours and the reaction was stopped.

The reaction mixture was then extracted three times with methylene chloride. The combined extract was then washed twice with saturated sodium hydrogen carbonate solution and further washed twice with saturated salt solution, and then dried over anhydrous magnesium sulfate, followed by condensation to remove the solvent. The remaining oily substance was then chromatographed on CC-7 silica gel (as described above) and eluted with a mixture of benzene-ethyl acetate (9:11 by volume) to obtain the compound (IIa) as a colorless oily substance. The following Table 1 shows the yields of several compounds (IIa) obtained according to this general procedure.

TABLE 1

| Type of aliphatic acid | Amount of aliphatic acid (mg) | Yield of IIa mg (%) |
| --- | --- | --- |
| trans-2-octadecenoic acid | 677 | 1.16 (77) |
| trans-2-heptadecenoic acid | 643 | 1.10 (74) |
| trans-2-hexadecenoic acid | 610 | 1.02 (70) |
| trans-2-pentadecenoic acid | 576 | 1.07 (75) |
| trans-2-tetradecenoic acid | 542 | 1.18 (84) |
| trans-2-tridecenoic acid | 509 | 1.26 (92) |
| trans-2-dodecenoic acid | 475 | 1.28 (95) |
| trans-2-undecenoic acid | 442 | 1.25 (95) |
| trans-2-decenoic acid | 408 | 1.16 (90) |
| trans-2-nonenoic acid | 374 | 1.04 (89) |
| trans-2-octenoic acid | 341 | 1.24 (93) |
| trans-2-heptenoic acid | 307 | 1.21 (95) |
| trans-2-hexenoic acid | 274 | 1.19 (95) |
| 3-methylcrotonic acid | 240 | 0.905 (78) |
| cis-2-undecenoic acid | 356 | 0.978 (74) |
| cis-2-tetradecenoic acid | 436 | 1.083 (74) |

EXAMPLE 7

15β-hydroxyailanthone-α,β-unsaturated carboxylic acid esters (IIb)

The compound (IIb) can be prepared from the above compound (IIa) by the following general procedure.

1.0 mM of the compound (IIa) obtained according to Example 6 was dissolved in a methanolic solution of 0.01N potassium methoxide. The resulting solution was then stirred for 2 hours under $N_2$ atmosphere. The reaction mixture was then adjusted to pH 4–5 with 1N HCl and thereafter the solvent was distilled off. The residue was then extracted three times with methylene chloride after the addition of water. The fractionated methylene chloride layers were washed twice with saturated aqueous saline and dried over anhydrous magnesium sulfate. The solvent was removed from the dried extract in vacuo and the residue thus obtained was chromatographed on silica gel (Kiesel gel-60, Merck, 70-230 mesh ASTM) and then eluted with the mixture of ethyl acetate-hexane (5:2 by volume) to give a pure compound (IIb). In addition, the mixture of monoacetate and diacetate fractionated by the above chromatography was re-acetylated with ten times amount of pyridine and twenty times amount of acetic anhydride at room temperature for 48 hours, and then hydrolyzed as in the above. Thus, the desired compound (IIb) can further be recovered.

The following Table 2 shows the yields of several compounds (IIb) obtained according to this general procedure.

TABLE 2

| Type of starting compound (IIa) | Yield of IIb (%) |
| --- | --- |
| trans-2-octadecenoate | 40 |
| trans-2-heptadecenoate | 42 |
| trans-2-hexadecenoate | 43 |
| trans-2-pentadecenoate | 40 |
| trans-2-tetradecenoate | 47 |
| trans-2-tridecenoate | 49 |
| trans-2-dodecenoate | 50 |
| trans-2-undecenoate | 51 |
| trans-2-decenoate | 54 |
| trans-2-nonenoate | 50 |
| trans-2-octenoate | 52 |
| trans-2-heptenoate | 44 |
| trans-2-hexenoate | 33 |
| trans-2-pentenoate | 34 |
| 3-methylcrotonate | 34 |
| cis-2-undecenoate | 40 |
| cis-2-tetradecenoate | 41 |

Antineoplastic Activity of the Compounds of Present Invention

Materials

Animals: Mouse ($BDF_1$, female, 4–5 weeks, average body weight: 18 g)
Cells: Mouse lymphocytic leukemia p388
Medicine: Compounds (IIb)(n=5(trans),6(trans), 7(trans),8(trans),9(trans),10(trans), 12(trans),14(trans),7(cis) and 10(cis))

Method $10^6$ cells of mouse lymphocytic leukemia p388 were intraperitoneally injected to $BDF_1$ mouse (6 mice per group). From the 2nd day after the injection, the destined amount of the medicine as shown in following Table 3 was administered for 5 days continuously. Thereafter, the surviving percentages (ILS) of the administered mice were calculated by the following equations.

TABLE 3

$$ILS = \frac{\text{Mean survival time of the administered group}}{\text{Mean survival time of the control group}} \times 100 - 100\%$$

| Medicine (IIb) | Dose (mg/kg) | | | | | |
| --- | --- | --- | --- | --- | --- | --- |
|  | 30 | 10 | 5 | 3 | 1 | 0.5 |
| n = 5(trans) | 84 | 55 | 37 | — | — | — |
| n = 6(trans) | 100 | 54 | 50 | — | — | — |
| n = 7(trans) | 80 | 74 | 69 | — | — | — |
| n = 8(trans) | 84 | 65 | 63 | — | — | — |
| n = 9(trans) | 86 | 64 | 46 | — | — | — |
| n = 10(trans) | 102 | 67 | 47 | — | — | — |
| n = 12(trans) | 78 | 51 | 45 | — | — | — |
| n = 14(trans) | 47 | 6 | 6 | — | — | — |
| n = 7(cis) | 66 | 54 | 39 | — | — | — |
| n = 10(cis) | 64 | 56 | 34 | — | — | — |
| control* | — | — | — | — | 83 | — |

*Mitomycin C was used as the positive control

As shown by the above Table 3, the compound (IIb) is markedly effective against mouse lymphocytic leukemia p338. Especially, the compound of n=6(trans) and n=10(trans) are so effective that they can prolong the life of the administered group as much as twice or more as compared to that of the control group and far more effective than that of known mitomycin C administered group. This fact will give a preferably aspect to the use of the compound of this invention as a novel antitumor agent.

While the invention has been described in detail and with reference to specific embodiment thereof, it will be apparent to one skilled in the art that various changes and modifications can be made therein without departing from the spirit and scope thereof.

What is claimed is:

1. Ailanthone derivatives represented by the formula:

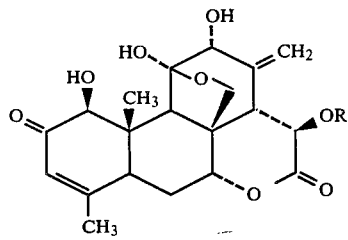

wherein R represents a member selected from the group consisting of a trans-2-decenoic acid residue, a trans-2-undecenoic acid residue and a trans-2-tetradecenoic acid residue.

2. The ailanthone derivatives according to claim 1, wherein R represents a member selected from the group consisting of a trans-2-decenoic acid residue and a trans-2-undecenoic acid residue.

* * * * *